United States Patent [19]
Bono

[11] Patent Number: 5,603,314
[45] Date of Patent: Feb. 18, 1997

[54] AEROSOL FILTRATION DEVICE AND INHALATION APPARATUS CONTAINING SAME

[76] Inventor: Michael Bono, 882 Black Rd., Collegeville, Pa. 19426

[21] Appl. No.: 409,190

[22] Filed: Mar. 22, 1995

Related U.S. Application Data

[63] Continuation-in-part of Ser. No. 409,259, Mar. 22, 1995.
[51] Int. Cl.$^6$ .................................................. A61M 16/00
[52] U.S. Cl. ........................... 128/200.21; 128/204.18; 128/205.12; 128/205.24; 128/910; 128/909; 128/200.14; 128/205.29
[58] Field of Search .................. 128/204.18, 205.12, 128/205.24, 911, 912, DIG. 26, 910, 909, 200.21, 200.18, 200.14, 205.29, 204.13

[56] References Cited

U.S. PATENT DOCUMENTS

| | | | |
|---|---|---|---|
| 4,094,317 | 6/1978 | Wasnich | 128/194 |
| 4,159,803 | 7/1979 | Cameto et al. | 239/102 |
| 4,177,945 | 12/1979 | Schwartz et al. | 239/338 |
| 4,190,046 | 2/1980 | Virag | 128/200.21 |
| 4,462,397 | 7/1984 | Suzuki | 128/911 |
| 4,462,399 | 7/1984 | Braun | 128/201.25 |
| 4,612,926 | 9/1986 | Boiarski et al. | 128/200.21 |
| 4,629,590 | 12/1986 | Bagwell | 261/78.2 |
| 4,767,576 | 8/1988 | Bagwell | 261/16 |
| 4,823,784 | 4/1989 | Bordoni et al. | 128/200.14 |
| 4,829,998 | 5/1989 | Jackson | 128/204.18 |
| 4,993,436 | 2/1991 | Bloom | 128/200.21 |
| 5,044,361 | 9/1991 | Werner et al. | 128/204.16 |
| 5,063,921 | 11/1991 | Howe | 128/200.14 |
| 5,186,166 | 2/1993 | Riggs et al. | 128/203.15 |
| 5,259,370 | 11/1993 | Howe | 128/200.14 |
| 5,301,662 | 4/1994 | Bagwell et al. | 128/200.14 |
| 5,335,860 | 8/1994 | Hieftje et al. | 239/469 |

FOREIGN PATENT DOCUMENTS

| | | | |
|---|---|---|---|
| 670977 | 6/1939 | Germany | 128/910 |

OTHER PUBLICATIONS

Atomic Products Corporation trade literature entitled "Venti-Scan II—Disposable Radioaerosol System For Ventilation Scanning Studies", Atomlab Division, Shirley, New York (undated).
Cadema trade literature entitled "AeroTech I—Aerosol delivery systems for improved imaging and controlled deposition of aerosol solutions", Cadema Medical Products, Inc. (undated).
Intenational CIS trade literature entitled "Venticis II—Lung Scintigraphy Without Constraint", Subsidiary of Compagnie ORIS Industrie S.A., Saint–Quentin–Yvelines Cedex, France (undated).
Medi Nuclear trade literature entitled "Aero/Vent—Lung Aerosol Delivery System", Medi Nuclear Corporation, Inc., Baldwin Park, California, Oct. 1988.
Mallinckrodt trade literature entitled "Radioaerosol Inhalation Imaging—An Emerging Choice for the Assessment of Pulmonary Function", Diagnostic Products Division of Mallinckrodt, Inc., St. Louis, Missouri (undated).
3M trade literature entitled "It's Not Just An Air Filter, It's An Obstacle Course", 3M Filtration Products, 3M Company, St. Paul, Minnesota, 1992.

*Primary Examiner*—V. Millin
*Assistant Examiner*—William J. Deane, Jr.
*Attorney, Agent, or Firm*—Duane Morris & Heckscher

[57] ABSTRACT

An improved filtration device suitable for reducing exhaled particles in an aerosol inhalation device. The filtration device includes a body portion having an interior chamber which communicates with an inlet and outlet opening through the chamber wall. Within the chamber is a substance recovery media designed to capture a portion of the exhaled particles from the patient and for assisting in returning a portion of the captured particles back to the patient, such as by a nebulizer. The filtration device further includes a filter layer located within the interior chamber for filtering out contaminants, such as viruses and bacteria, in the gaseous medium prior to releasing the remaining portion of the gaseous medium into the environment. Aerosol inhalation devices containing such filters are also provided by this invention.

20 Claims, 4 Drawing Sheets

AEROSOL FILTRATION DEVICE AND INHALATION APPARATUS CONTAINING SAME

CROSS REFERENCE TO RELATED APPLICATIONS

This application is a continuation-in-part of U.S. patent application Ser. No. 409,259, filed on Mar. 22, 1995, and entitled "AEROSOL INHALATION DEVICE CONTAINING A RAIN-OFF CHAMBER."

FIELD OF THE INVENTION

This invention relates to methods of producing aerosols for patients, and in particular, to apparatus for improving the delivery of aerosol therapeutics and diagnostics.

BACKGROUND OF THE INVENTION

Aerosol inhalation equipment is often used in medical facilities for generating aerosol mists for diagnostic and therapeutic procedures. Such devices are especially useful in pulmonary therapy for pneumonia and for introducing radioactive vapors foe diagnosing diseases.

The engine of most aerosol-generating equipment is the nebulizer, a device which mixes pressurized air or oxygen with diagnostic or therapeutic fluids to create an aerosol mist. During operation, the liquid to be aerosolized is placed in a liquid reservoir in the nebulizer. Air under pressure enters the system and acts to draw the liquid up a delivery tube to an aerosol exit orifice, similar to a jet pump. At the aerosol exit orifice, the fluid is atomized into a fine mist. Larger drops that are produced in the mist impinge on baffles above the aerosol exit orifice where they drain back into the reservoir of the nebulizer. Smaller drops are entrained by the air and are carried through the delivery system to the patient's lungs. A typical nebulizer is disclosed in Bordoni et al., U.S. Pat. No. 4,823,784.

The overall effectiveness of a nebulizer depends largely upon the distribution and size of the droplets produced. Droplets larger than 3.5 micrometers generally do not leave the nebulizer and run back into the bowl to be atomized again. Droplets between about 1.5 and 3.5 micrometers often collect on the walls of the delivery system and frequently settle onto the lips, mouth, or bronchial tubes of the patient without ever reaching the alveolar, often referred to as the "deep lung".

A 1987 study performed on one aerosol inhalation system indicated that only 25% of the liquid initially charged into the nebulizer actually reached the patient's lungs during a seven minute exposure. Typically, only 66% of this amount actually remains in the deep lung of the patient; the other 33% is exhaled. Therefore, only about 16% of the liquid therapeutic or diagnostic substance charged to the nebulizer is ever used by the patient. The remainder is wasted, or winds up contaminating the environment. Consequently, much of the liquid charge loaded into the nebulizer is provided only to ensure that a proper dose can be received in a reasonable exposure time.

Since most aerosol inhalation devices are currently made for one-time patient use, and are thereafter disposed, any medication or diagnostic fluid remaining in the device becomes waste. Nevertheless, decreasing the amount of fluid required for delivering a prescribed amount to a patient's lung while increasing the delivery efficiency of the fluid has been hard to achieve. With respect to radioactive therapeutics and diagnostics, there is also a great need to decrease the treatment times so as to minimize radiation doses to both the patient and nearby healthcare workers.

Despite these recognized deficiencies of current nebulizer devices, there has been very little improvement in the actual performance of modern systems. Most of the more recent variations have been in the nebulizer design, such as the placement of baffles, variations in orifice size and other structural elements which are somewhat unrelated to increased delivery. There has been very little research conducted to improve the particle size distribution and control through nebulization techniques rather than through baffling. There has also been few changes made in the recovery of medication and trapped moisture to reduce waste, and to improve production efficiency.

Even though modern investigators have presently correlated the mass-median-drop size (MMD) produced by a nebulizer to the properties of the liquid and the delivery system, there is currently no way to account for the effect of structural variations on the drop size produced. Moreover, previous studies have also shown that various commercial nebulizers produce essentially the same aerosol, but the structural differences between the nebulizers, such as the addition and placement of a baffle, caused selective losses of larger particles. This method of drop size reduction, by itself, is generally unsatisfactory and inefficient because the drop size is reduced at the expense of reducing the rate of drug delivery.

SUMMARY OF THE INVENTION

This invention provides in a first embodiment a filtration device suitable for reducing exhaled particles released by a patient during aerosol inhalation therapy. The device includes a body portion having an interior chamber and inlet and outlet openings. Within the chamber is a substance recovery media designed to capture a portion of the exhaled particles and to assist in returning a portion of these captured particles back to the patient. Also included is a filter layer located within the interior chamber for screening out contaminants in the gaseous medium prior to releasing a remaining portion of this gas into the environment.

Accordingly, this filter device can be used as a passive humidifier designed to capture the heat and moisture lost during exhalation and return it to the patient during inhalation. The disclosed substance recovery media can achieve extremely high moisture output with low resistance, and can be made from salt-free fibers, which are known to leach out and corrode inhalation equipment. Moisture output from the preferred substance recovery media of this invention has been measured to be greater than 28 mg/l $H_2O$ with a resistance of less than 2.8 cm $H_2O$ at 60 l/m.

In a more preferred embodiment of this invention, an aerosol inhalation device is provided for delivering aerosol mist to a patient. The device includes proximal and distal ends and a nebulizer for generating an aerosol containing droplets of a first liquid. This device also includes first and second conduits for providing passage of an aerosol to and from a patient. Any gaseous medium containing exhaled droplets from the patient is thereafter delivered to filtration means for capturing a portion of the exhaled droplets while permitting a gas contained within the gaseous medium to pass through an exhaust port.

The inhalation device of this invention utilizes a substance recovery media to make more efficient use of aerosolized substances, such as valuable therapeutic and diagnostic medicaments, that would usually be wasted or could leak out into the hospital environment. The filtration devices of this invention can be used to recover and return back to the nebulizer, liquid droplets of these substances for regeneration into a therapeutic or diagnostic aerosols. Additionally, a filter layer can be used in conjunction with the substance recovery media to reduce bacterial or viral particles in the gaseous exit stream. In a most preferred embodiment, this filter includes a thermoplastic seal around its circumference for reducing the leakage of radioactive contamination, bacteria, or viruses, for example, that would otherwise pass around the filter during normal use. The filter preferably has the ability to electrostatically attract particles in the range of about 0.3–7 micrometers at face velocities of at least about 20 and up to about 100 fpm. The preferred filter achieves an efficiency of greater than 90%, and preferably of at least 95%, of particles within that range with a pressure drop of less than about 25 mm $H_2O$.

A BRIEF DESCRIPTION OF THE DRAWINGS

The accompanying drawings illustrate preferred embodiments of the invention, as well as other information pertinent to the disclosure, in which:

FIG. 1: is a side elevation view of a preferred aerosol inhalation device of this invention, illustrating some of the more important connections and features in phantom, and the substance recovery media in cross-section;

FIG. 2: is a top planar view of the aerosol inhalation device of FIG. 1;

FIG. 3: is a side elevation, exploded view of the proximal end of the aerosol inhalation apparatus of FIG. 1; and FIG. 4: is a side elevation, cross-sectional view of a preferred nebulizer design for use in connection with the preferred aerosol inhalation apparatus of FIG. 1.

DETAILED DESCRIPTION OF THE INVENTION

Improved nebulizers for creating aerosol mists and aerosol inhalation devices containing these nebulizers are provided by this invention. These devices employ improved nebulization techniques for providing increased sheer action during atomization of therapeutic and diagnostic fluids so that a greater delivery rate of smaller liquid droplets are provided to the deep lung of patients.

Figure 1:
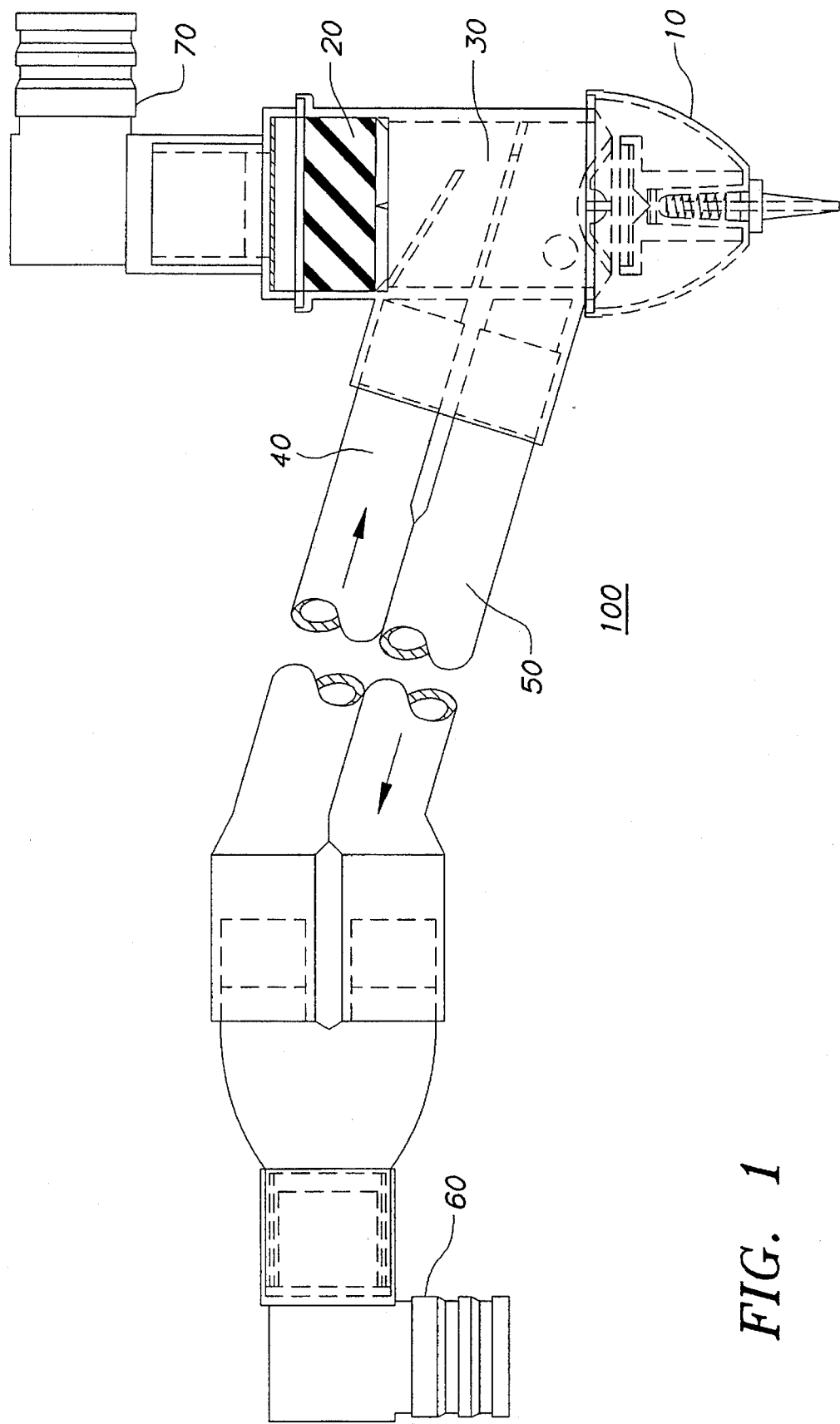
Figure 2:
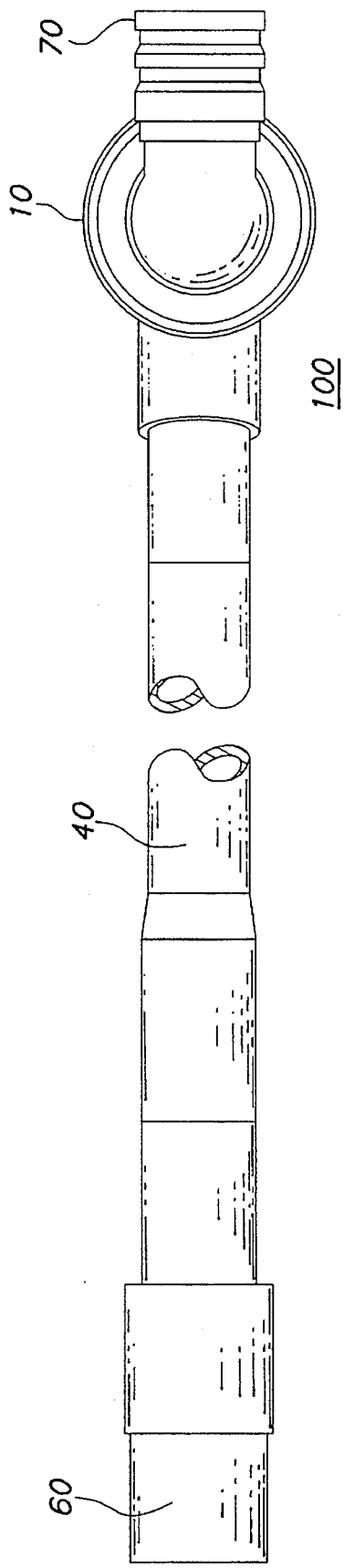
Figure 3:
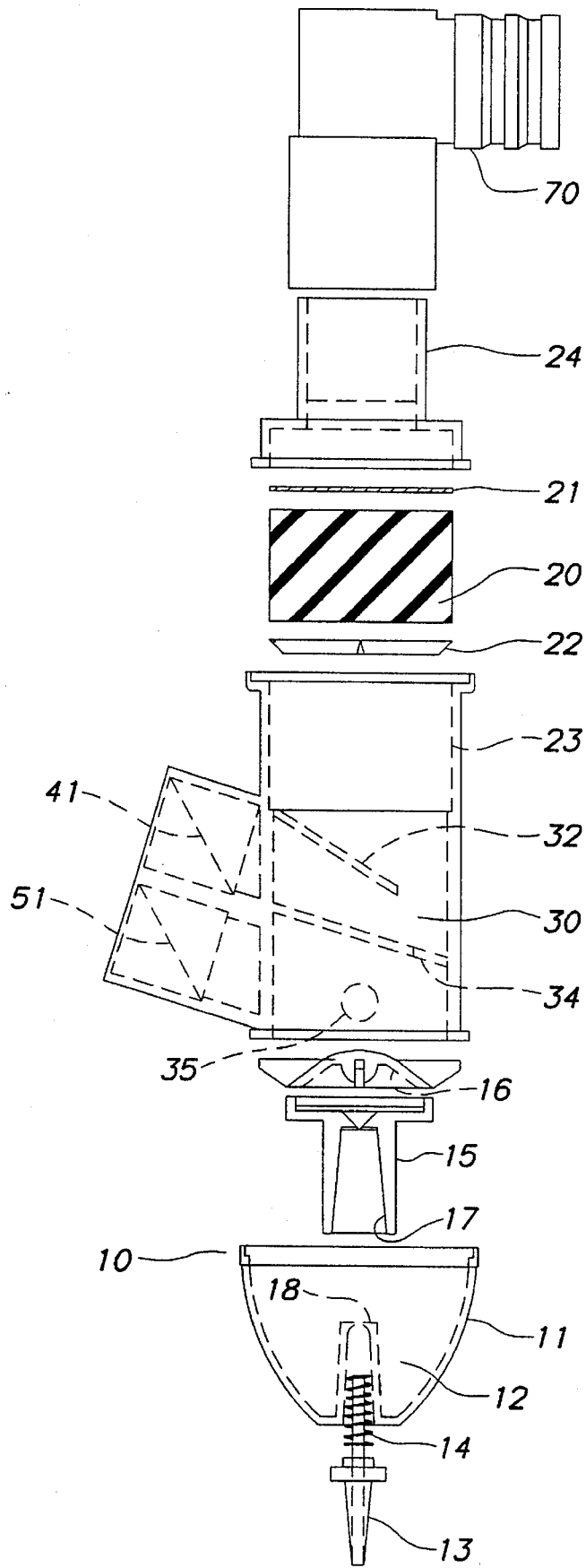

With respect to the figures and particularly with respect to FIGS. 1–3 thereof, there is shown a preferred aerosol inhalation device. This device 100 contains some basic elements which represent groups of constituent parts that are labeled together for convenience. These elements include a nebulizer 10 for producing an aerosol and an exhaust port 70 for exit gases, a form of substance recovery media 20, and a rain-off chamber 30 which helps to contain humidity and recycle expensive therapeutic and diagnostic fluids back into the nebulizer 10. As the patient breathes through a mouthpiece attached to the fitting 60 located at the distal end of the device 100, aerosol mist and compressed air are received through one-way valve 51 and aerosol conduit 50. As the patient exhales, one-way valve 51 closes, one-way valve 41 opens, and exhaust gases are channeled through exhaust conduit 40 into the rain-off chamber 30 where aerosol, water vapor, liquid and gases are separated. Liquid constituents are returned to the nebulizer by gravitational force, exhaust gases are discharged, and any left-over aerosol is temporarily stored in the chamber 30. When the patient inhales a second, or subsequent, time, droplets contained within the substance recovery media 20 are returned to the nebulizer or are returned back to the patient through one-way valve 51. The operational parts of these basic elements will now be described in more detail.

With reference to the exploded view of FIG. 3, compressed air or oxygen is typically received through the gas inlet 13 at the proximal end of the nebulizer 10. A compressor can be attached to the nipple of the gas inlet 13 to generate a source of compressed air at a pressure of about 35–50 psi and a flow rate of less than about 10 liters per minute, and preferably about 6 liters per minute.

Figure 4:
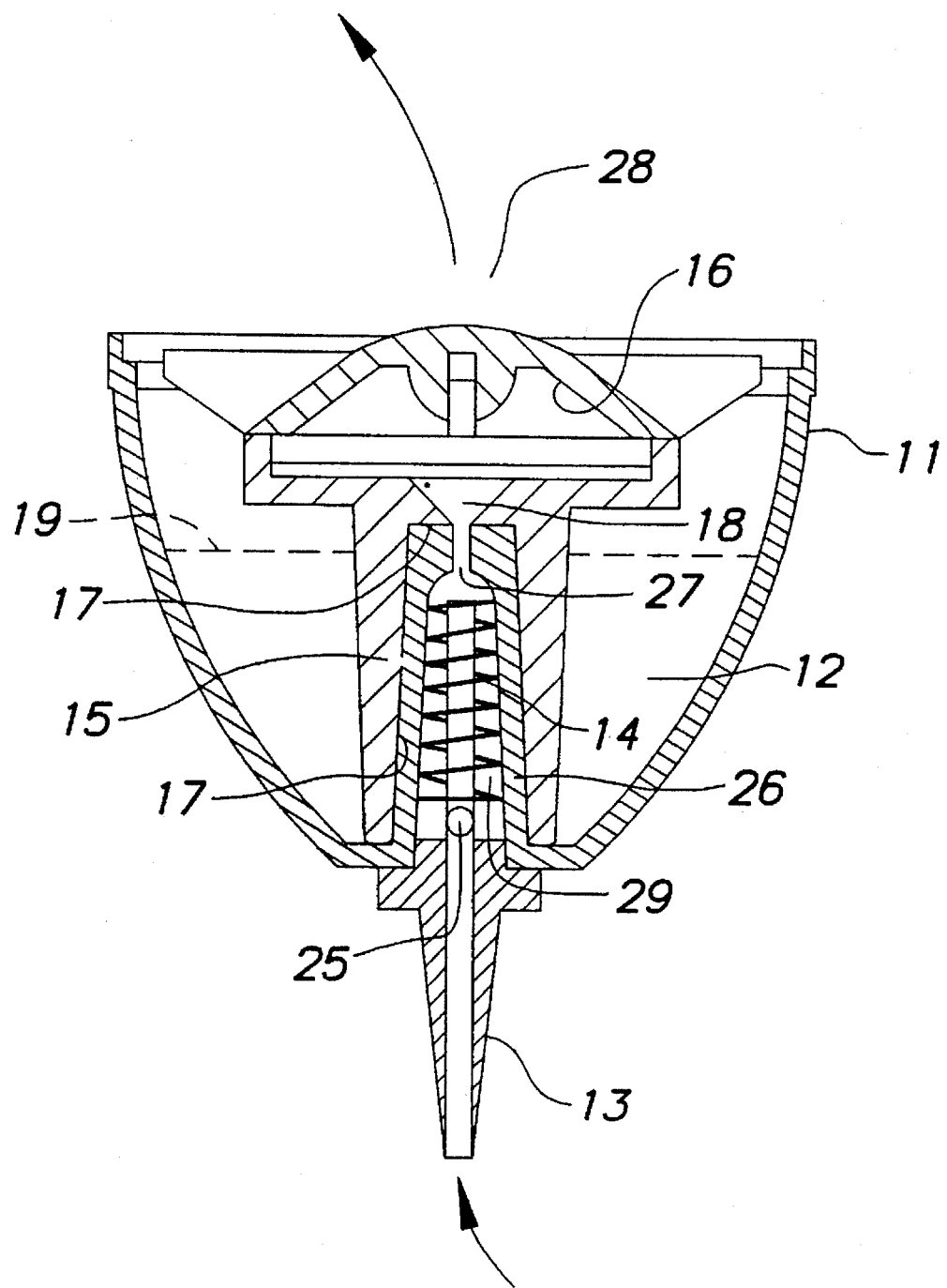

Once the air comes through the gas inlet 13 and through gas channel inlet orifice 25, it contacts a gas flow control device, which in the preferred embodiment, provides both an axial jet velocity and a tangential velocity to the gas. This can be accomplished by a combination of a swirler 14 and gas channel wall 26, shown more clearly in FIG. 4. The swirler 14 preferably consists of a spiral air passage, although there are many other ways to produce a swirling action, such as by employing vanes, a propeller-device, or inner helical grooves mounted within the gas channel wall 26.

The gas channel wall 26 preferably is in the shape of a venturi tube so as to provide an axial jetting velocity to the compressed gas. When the swirler 14 and venturi tube are used together, a high delivery rate aerosol can be produced because the normal breakup of liquid caused by the axial jetting action is enhanced by the swirling air flow, and more shearing forces are created, providing more efficient atomization. The result is that more smaller drop sizes are produced at the same overall liquid delivery flow rates as provided by existing nebulizers.

The nebulizer 10 also includes a bowl housing 11 for containing a liquid reservoir 12. The liquid reservoir is charged to a liquid level 19 located below the deflector dome 16. As compressed air flows through the gas channel 29 formed between the gas channel wall 26 and swirler 14, it is deflected by the helical ridges of the swirler 14 in a tangential direction to produce a tangential velocity element to the jet flow. The swirling gases then exit at the gas channel exit orifice 27 and create a venturi vacuum. This vacuum, in turn, draws liquid from the liquid reservoir 12 through liquid channel 17 formed between liquid channel insert 15 and gas channel wall 26, which mixes with the swirling gas jet at the liquid channel orifice 18 to form an aerosol.

Within a fraction of a second, the aerosol contacts the lower surface of the deflector dome 16, which collects droplets larger than about 3–3.5 micrometers and returns them back into the liquid reservoir 12 along the wall of the bowl housing 11, so that they can be atomized later. Particles between about 1.5 and 3.5 micrometers can also collect along the bowl housing 11 and be returned in similar fashion. The aerosol, thus produced, exits the aerosol outlet 28 and is channeled through the one-way valve 51 into the aerosol conduit 50 and to the patient. Injections of additional liquid, or an additional substance, can be delivered into the liquid reservoir through injection port 35.

The aerosol produced by the nebulizer 10 of this invention preferably has an increased delivery rate of liquid drops within the size range of about 0.5–1.5 micrometers. One way of measuring the delivery rate is to pass a laser light beam, infrared radiation or an equivalent radiation source through a cloud produced by the aerosol and measure the amount of light that passes through the mist with a light detector. The reading for the amount of light that is obscured by the mist is called the "obscuration rating" of the aerosol and is directly related to the aerosol's delivery rate. The aerosols of this invention have a preferred obscuration rating of at least 10% even though they can simultaneously produce a median droplet size of less than one micrometer. This has not been accomplished in prior art devices because baffling techniques alone only serve to reduce the number of larger particles at the expense of delivery rate and obscuration rating. This is shown by the MICROCIRRUS device listed in Table 1. Current nebulizers have succeeded in improving the obscuration rating only by allowing more droplets of greater sizes to pass from the nebulizer, as illustrated by the data for the ULTRAVENT commercial nebulizer in Table 1 below. Amici's novel VENTISOL device, has succeeded in maintaining a large number of small droplets, while at the same time delivering a large volume of liquid with a high obscuration rating. A comparison of all three products is reflected below.

Acceptable substance recovery materials include polymer- or natural fiber-based moisture exchange media, such as HME media produced by 3M. HME media can achieve an extremely high moisture return rate with low resistance to exiting gases. It is salt-free, so it does not leech out salts that can corrode the equipment or be recycled back into the nebulizer. It comes in thicknesses of about 18–24 mm, has a moisture output of greater than 28 mg/l at 500 ml tidal volume, and exhibits a resistance to flow of up to 2.8 cm $H_2O$ at 60 l/m.

The preferred substance recovery media 20 is disposed below a recovery media cap 24 and is sandwiched between filter 21 and snap ring 22, although it is envisioned that the filter 21 could be located more distally or proximally in the inhalation device.

The preferred filter 21 consists of thermoplastic strands of woven or non-woven material which are layered to acquire

TABLE 1

| | Comparison of Aerosols of Competitive Devices | | | | | |
|---|---|---|---|---|---|---|
| | Obscuration | Median Droplet Size (50%) | % of Droplets Between .2–.48 μm | % of Droplets Between .48–.59 μm | % of Droplets Between .59–.71 μm | % of Droplets Between .71–.86 μm | % of Droplets Below 1.04 μm |
| MICROCIRRUS | 8.66% | .64 μm | 15.62 | 23.11 | 23.24 | 17.44 | 90.2 |
| ULTRAVENT | 18.97% | 1.02 μm | .03 | 5.72 | 11.55 | 15.83 | 52.0 |
| VENTISOL | 21.04% | .62 μm | 21.37 | 23.07 | 21.46 | 15.38 | 90.56 |

The preferred substance recovery media section of this invention will now be described. In certain medical breathing applications, moist air is added to the breathing circuit to prevent the patient's lungs from drying out. Since patients exhaust moisture, there is already a source of humidity available within the closed system which can be used to remoisturize a patient's own lungs. This invention provides a substance recovery media 20 located in the proximal end of the aerosol inhalation device 100, preferably between the rain-off chamber 30 and exhaust port 70.

The substance recovery media 20 should be able to achieve high moisture output with low resistance to exhaust gases. It is also desirable that it be salt- and toxic-free. The preferred substance recovery media 20 contains a fibrous material having a plurality of air channels formed therein for attracting liquid onto the fibers, while permitting gas to flow through. Such material should be able to recover moisture, including therapeutic and diagnostic liquids, as well as water vapor exhausted by the patient.

With respect to FIG. 3, the operation of the preferred rain-off chamber 30 in combination with the substance recovery media 20 will now be described. As the patient exhales, exhaust gases, including entrained medications, diagnostics, mucous, or water vapor are delivered through one-way valve 41 and into chamber 30. Liquid droplets in the gas are then tapped by the substance recovery media 20 while the gas exits exhaust port 70. Liquids collecting on the chamber walls can be returned back through the rain-off return 34 into the nebulizer 10, where they can be reatomized. Any remaining water vapor or entrained medicine in the chamber 30 can be reinhaled by the patient, back through rain-off return 34 through one-way valve 51. This process can be assisted by ambient air received through the exhaust port 70, which helps to push stalled vapors in the chamber 30 and collect and blow back captured droplets from the substance recovery media, and deliver these liquid and vaporous substances back to the patient.

a desired filtration density of 30–300 g/cm³, preferably about 200 g/cm³. The thermoplastic preferably is polypropylene or polyethylene, although many other polymers would be suitable.

The filter 21 can be die cut into a desired shape to fit the substance recovery form, recovery media cap 24, or both. The filter 21 should be of sufficient size and density to prevent the penetration of vapors, toxins, viruses etc., from exiting exhaust port 70. It can be electrostatically charged to a charge density within the range of 10–125 nC/cm², or at least about 50 nC/cm², and preferably about 75 nC/cm², or treated to be hydrophilic or hydrophobic depending on the end use for the material. One preferred filtration media is a product manufactured by 3M under the trademark FIL-TRETE.

In an important aspect of the filter 21 of this invention, a seal of less than about 0.25 inch in width is provided around the filter's outer periphery. In a preferred embodiment the filter 21 can be sealed by such methods as heat sealing, ultrasonic sealing, or by applying pressure to melt the thermoplastic strands along the edge of the filter 21 to form a relatively solid mass. The filter 21 can also be sealed to fit within holding frames, filter shelves or other mechanisms to give it strength and shape to satisfy a particular filtration requirement. Other methods of sealing the periphery of the die cut edge of the filter can include using adhesive sealing materials such as wax, varnish, epoxy, or glue that would solidify the die cut edge and create a water, air flow, and vapor seal.

In many prior art filter devices, holding frames and shelves are designed with edge clamps which mechanically retain a filter in place, but allow vapor and other contaminants to pass around the die cut limits of the filter. By providing a positive adhesive or melted seal around the filter, such vapor leaks are substantially eliminated.

The sealed edge filter of the preferred embodiment has application outside of the nebulizer field, and can be useful in many applications where particle capture is critical and space is at a premium. Such applications include ventilation systems, air purifiers, air conditioners, computers, vacuum cleaners, copying machines, laser printers and other equipment. In the medical field, applications include breathing circuits, spirometers, incubator filters, radioaerosol moisture trapping devices and similar apparatus.

The rain-off chamber 30, described above, can be fabricated within the body 23 of the aerosol inhalation device 100. As shown in FIG. 3, the body 23 is preferably located between the nebulizer 10 and the substance recovery media 20. The rain-off chamber 30 is desirably positioned proximally from one-way valve 41, and one-way valve 51. During use, aerosol enters in the lower half of the rain-off chamber 30 from the nebulizer 10 and is directed through one-way valve 51 into the aerosol conduit 50 for patient use. When the patient exhales, exhaust gases and leftover aerosol vapor travel down exhaust conduit 40, through one-way valve 41, and back into the upper portion of the rain-off chamber 30. The gases, with their entrained vapors, contact the inner surfaces of the rain-off chamber 30, and the larger droplets accumulate immediately upon exhaust deflector 32 and the far wall of rain-off chamber 30. Since nearly 66% of the total amount of aerosol inhaled by the patient is passed through the exhaust conduit 40, the rain-off chamber 30 can be important in order to recycle and conserve expensive diagnostic and therapeutic liquids. When these vapors come in contact with the inner surfaces of the rain-off chamber, they condense or bead up onto the surfaces and are fed by gravitational forces downward through the rain-off return 34 and back into the liquid reservoir 12 of the nebulizer 10.

In a preferred embodiment of the rain-off chamber 30, a significant portion of the interior surfaces of this chamber 30 is hydrophobic, in that the liquid contact angle of droplets on these surfaces is less than about 90 degrees. Stated differently, the rain-off surfaces preferably have a critical surface tension of less than about 40 dynes/cm, and more preferably less than about 32 dynes/cm. Hydrophobic polymers, ceramics, cellulosic and metallic materials or other materials which have been coated to be hydrophobic can be used. Suitable materials include polyethylene, polypropylene, fluorocarbons, silicones and the like. One commercial resin that has proved to be acceptable is Exxon's Exact Resin No. 4024. Silicone rubber and polyethylene, however, appear to show the greatest promise in recycling aerosol products.

From the foregoing, it can be realized that this invention provides improved nebulizers and aerosol inhalation apparatus that contain them. These nebulizers can increase the rate of delivery of efficacious aerosol mists to the deep lung of patients by using improved nebulization techniques. Additionally, improved rain-off techniques are used to recirculate valuable therapeutic and diagnostic fluids for reatomization, and more effective substance recovery and filtration designs are disclosed for protecting the environment and returning liquid and liquid vapor back to the nebulizer or patient. Although various embodiments have been illustrated, this is for the purpose of describing, and not limiting the invention. Various modifications, which will become apparent to one skilled in the art, are within the scope of this invention described in the attached claims.

What is claimed is:

1. An aerosol inhalation device for delivering an aerosol mist to a patient, comprising:

a nebulizer for generating an aerosol containing droplets of a first liquid;

a first conduit connected to said nebulizer for providing passage of said aerosol to said patient;

a second conduit for providing passage of a gaseous medium exhaled from said patient, said gaseous medium containing exhaled droplets of said first liquid;

an exhaust port located proximally from said second conduit; and filtration means located between said second conduit and said exhaust port for capturing a portion of said exhaled droplets and recycling said portion back to said nebulizer upon inhalation by said patient while permitting a gas contained within said gaseous medium to pass through to said exhaust port.

2. The aerosol inhalation device of claim 1, wherein said filtration means is disposed above said nebulizer in said device.

3. The aerosol inhalation device of claim 1, wherein said filtration means comprises a porous polymer fiber material.

4. The aerosol inhalation device of claim 2, wherein said filtration means comprises a substance recovery media and a filter.

5. The aerosol inhalation device of claim 3, wherein said substance recovery media comprises means for assisting in returning a portion of said exhaled droplets to said aerosol.

6. The aerosol inhalation device of claim 4, wherein said substance recovery media is ionically charged.

7. The aerosol inhalation device of claim 6, wherein said filter has a sealed peripheral edge and substantially prevents the passage of particles electrostatically with very little pressure drop.

8. The aerosol inhalation device of claim 1, further comprising a rain-off chamber located between said second conduit and said filtration means, said rain-off chamber having a liquid contact surface therein for collecting a portion of said exhaled droplets and returning them to said nebulizer.

9. The aerosol inhalation device of claim 8, wherein said rain-off chamber is disposed to receive a plurality of liquid droplets captured by said filtration means.

10. An aerosol inhalation device for delivering an aerosol mist to a patient comprising:

a nebulizer for generating an aerosol containing droplets of a first liquid;

a first conduit connected to said nebulizer for providing passage of said aerosol to said patient;

a second conduit for providing passage of a gaseous medium exhaled from said patient, said gaseous medium containing exhaled droplets of said first liquid;

an exhaust port located proximally from said second conduit; and filtration means located between said second conduit and said exhaust port for capturing a portion of said exhaled droplets and recycling said portion back to said nebulizer upon inhalation by said patient while permitting a gas contained within said gaseous medium to pass through to said exhaust port, said filtration means containing a filter for removing contaminant particles of about 0.3–7 micrometers within said gaseous medium with an efficiency of at least about 90% and a pressure drop of no more than about 25 mm $H_2O$.

11. The aerosol inhalation device of claim 11, wherein said filter comprises thermoplastic fibers.

12. The aerosol inhalation device of claim 11, wherein said filter comprises a sealed edge.

13. The aerosol inhalation device of claim 11, wherein said filter comprises a relatively solid polymeric seal around its periphery.

14. The aerosol inhalation device of claim 11, wherein said filtration means further comprises a substance recovery media and said filter is located proximally from said substance recovery media and distally from said exhaust port.

15. The aerosol inhalation device of claim 10, wherein said nebulizer comprises a liquid reservoir for containing said first liquid, and said filtration means is disposed above said liquid reservoir in said aerosol inhalation device so as to permit a portion of said captured exhaled droplets to be returned to said reservoir upon inhalation by said patient.

16. The aerosol inhalation device of claim 15, further comprising a rain-off chamber disposed between said liquid reservoir and said filtration means.

17. A method of providing an aerosol mist to a patient, comprising:

providing an aerosol inhalation device which includes, a nebulizer for generating an aerosol containing droplets of a first liquid, a first conduit connected to said nebulizer for providing passage of said aerosol to said patient, a second conduit for providing passage of a gaseous medium exhaled from said patient, said gaseous medium containing exhaled droplets of said first liquid, an exhaust port located distally from said second conduit, and filtration means located between said exhaust port and said second conduit for capturing a portion of said exhaled droplets while permitting a gas contained within said gaseous medium to pass through to said exhaust port;

inserting a distal portion of said aerosol inhalation device into a breathing passage of said patient;

permitting said patient to inhale said aerosol;

recycling a portion of said exhaled droplets from said filtration means back to said nebulizer upon inhalation by said patient; and reatomizing said recycled portion of droplets.

18. A filtration device suitable for reducing a number of exhaled particles in an exhaled gaseous medium in an aerosol inhalation device, comprising a body portion having an interior chamber, inlet and outlet openings, a substance recovery media located within said interior chamber for capturing a portion of said exhaled particles and for assisting in returning a portion of said captured particles to said patient, and a filter layer located within said interior chamber and completely sealed around its periphery for screening out contaminants in said gaseous medium prior to releasing a remaining portion of said gaseous medium into the environment.

19. The filtration device of claim 18 wherein said filter layer comprises a heat sealed edge.

20. The filtration device of claim 19 wherein said sealed edge comprises a relatively solid polymer portion.

* * * * *